United States Patent [19]

Schuss et al.

[11] 4,398,886

[45] Aug. 16, 1983

[54] ROTATABLE SOCKET FOR A DENTAL HANDPIECE

[75] Inventors: Werner Schuss, Heppenheim; Johann Hain, Laudenbach, both of Fed. Rep. of Germany

[73] Assignee: Siemens Aktiengesellschaft, Berlin & Munich, Fed. Rep. of Germany

[21] Appl. No.: 310,285

[22] Filed: Oct. 9, 1981

[30] Foreign Application Priority Data

Oct. 28, 1980 [DE] Fed. Rep. of Germany ....... 3040537

[51] Int. Cl.³ .............................................. A61C 1/14
[52] U.S. Cl. .................................. 433/128; 279/1 E
[58] Field of Search ............... 433/126, 127, 128, 129; 279/1 E

[56] References Cited

U.S. PATENT DOCUMENTS

| | | |
|---|---|---|
| 1,853,089 | 4/1932 | Skinner .............................. 433/128 |
| 2,801,111 | 7/1957 | Kaltenbach .......................... 279/79 |
| 2,895,738 | 7/1959 | Baker .................................... 279/1 |
| 3,321,209 | 5/1967 | Sanders ................................ 279/23 |
| 3,325,899 | 6/1967 | Staunt .................................... 32/27 |
| 4,014,099 | 3/1977 | Bailey .................................... 32/27 |

FOREIGN PATENT DOCUMENTS 2822708 12/1978 Fed. Rep. of Germany .
891672 12/1943 France .
1127453 9/1968 United Kingdom .

Primary Examiner—Robert Peshock
Attorney, Agent, or Firm—Hill, Van Santen, Steadman, Chiara & Simpson

[57] ABSTRACT

A rotatable socket for supporting a tool for rotating in a head housing of a dental handpiece, includes a catch device which includes at least one catch member movable between a locking position for retaining a tool in the socket and an unlocking position for releasing the tool and a thumb actuated purchase. The purchase has a pressure surface that is movable from a position disengaged from each catch member to a position engaging each catch member, a cover member having a peripheral edge that is rigidly secured to the head housing, and the cover member has an elastically deformable portion movable through a stroke when pressure is applied to the purchase so that the deformable portion of the cover member will move through the stroke to cause the pressure surfaces to move each catch member to an unlocking position to release the tool from the socket.

12 Claims, 7 Drawing Figures

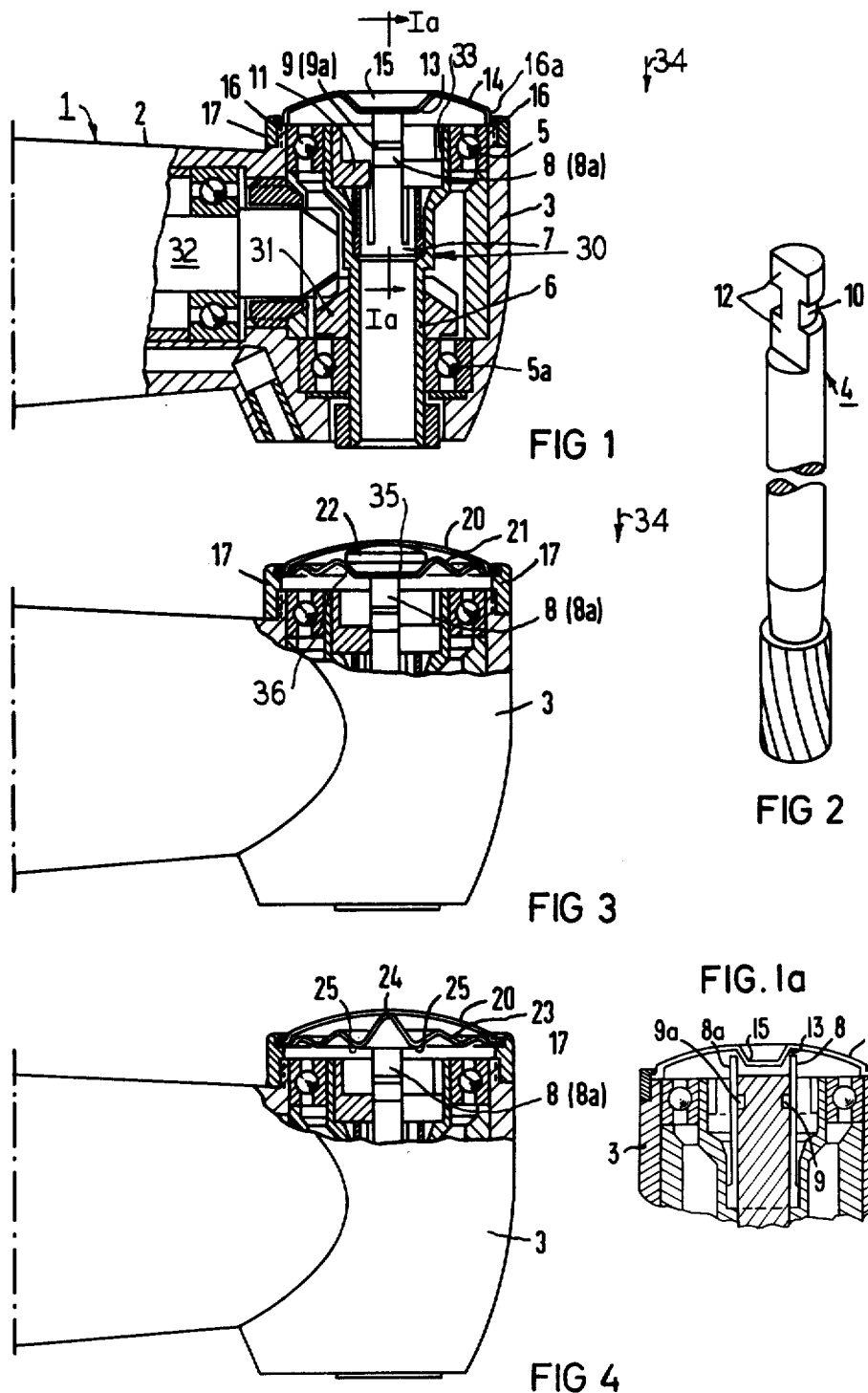

ROTATABLE SOCKET FOR A DENTAL HANDPIECE

BACKGROUND OF THE INVENTION

The present invention is directed to a socket for rotatably supporting a tool in a head housing of a dental handpiece which socket includes a catch means or device having at least one catch member which releasably locks a tool in the socket and is moved to an unlocking position by a thumb actuated purchase so that the tool may be removed from the socket.

Various systems are known for retaining or chucking dental tools in a socket of a dental handpiece. Thus, for tools which have cylindrical shanks, there are two known types of chucks, one is a friction chuck and the other is a screw chuck. An example of a friction collet is disclosed in U.S. Pat. No. 3,321,209. In this device, the collet has a sleeve which has been slotted to provide resilient tongues which are bent towards the center of the collet when in an idle state. When a tool shank is inserted, these resilient tongues are bent from their idle position and apply a gripping force to the shank. In order to remove the tool, the tool must usually be withdrawn or respectively ejected from the chucking device with the assistance of the special pressure or thrust tools. Insofar as it is carried out manually, the insertion and also the removal of the tool requires an exertion of great forces and requires special auxiliary devices such as drill ejector devices. Therefore the chucking and unchucking operation becomes relatively involved.

An example of the screw collet chuck is provided in U.S. Pat. No. 3,325,899. In this device, a separate auxiliary tool or wrench is required for securing and loosening the collet chuck.

In addition to tools which have cylindrical shanks, there are also tools which have an annular groove and a flattened portion adjacent or at the end of the cylindrical shank. The flattened portion can be brought into engagement with the dog in the hollow shaft of the socket to transmit torque therebetween. An example of a tool with an appropriate retaining device is disclosed for example in the earlier filed U.S. patent application Ser. No. 248,863 filed Mar. 30, 1981 and assigned to the assignee of the present application. In order to release the retaining element to enable an axial removal of the tool, a thumb actuatable purchase is tiltably seated at an upper end of the head housing which faces away from the neck part of the handpiece. In order to obtain a sufficient stroke to enable opening the retaining elements, it is necessary that the other end of the purchase which lies opposite the tilt position has sufficient movement. In two additional embodiments, which are disclosed in the above mentioned patent applications, the purchase, which is also loaded by a separate positioned spring, contains edge parts which are directed either towards the outside or respectively towards the inside and which coact with overlapping edge parts of the head housing to connect the purchase to the housing with the desired movement. Hereto, sufficient play must be provided between the head housing and the edge parts of the purchase so that the necessary stroke which is required for opening the retaining elements can be achieved.

SUMMARY OF THE INVENTION

The present invention is directed to providing an improved catch means for a rotatable socket, which rotatably supports a tool in the head housing of a dental handpiece. The catch means is suitable for all chucking and respectively retaining systems and wherein pressure is applied on a purchase of the catch means, a release of the parts, which is otherwise engaged with the tool without the assistance of a separate auxiliary tools, will occur. Moreover, the present invention provides for a simplification of the thumb actuatable purchase which has been earlier proposed which simplification includes both the fabrication of the purchase as well as providing a termination for the head housing which is largely dirt free.

To accomplish these goals, the present invention is directed to an improvement in a rotatable socket for rotatably supporting the tool in a head housing of a dental handpiece, said socket having catch means, which include at least one catch member, that movable between a locking position for retaining the tool in the socket and the unlocking position for releasing the tool, and a thumb actuated purchase disposed on the head housing, said purchase upon actuation engaging each catch member to move it to the unlocking position to release the tool and to allow its removal from the socket. The improvement comprises the purchase having a pressure surface movable from a position disengaged from each catch member to a position engaging each catch member to cause movement to the unlocking position, a cover member having a peripheral edge, and means for rigidly securing the peripheral edge of the cover member to the head housing, said cover member having an elastically deformable portion movable through a stroke while pressure is applied to the purchase so that upon applying pressure to the cover member, the deformable portion moves through the stroke to cause said pressure surface to move each catch member to the unlocking position.

Preferably the cover member has a circular periphery surrounding a dome portion which dome portion includes the elastically deformable portion and the cover member is mounted on the head housing with the dome part in its initial position being a convex sperical dome. The cover member has a spring like property so that on applying pressure to the convex spherical dome, it is converted into a concave spherical dome which urges the pressure surface to engage the catch members. Preferably, the spring-like property of the material of the cover member is such that upon release of the pressure, the spring nature of the material will cause the concave dome to snap back into the convex dome.

The cover member may have a central portion formed as an indentation which identation provides the pressure surfaces. In another embodiment, the pressure surfaces may be provided on an intermediate element such as a corrugated spring whose corrugation provides the pressure surface for engaging the catch means. To transfer movement of the cover member to the corrugated spring, a coupling element may be provided or the corrugated spring can have an enlarged centrally disposed dimple. In both these two examples, the cover member has an annular peripheral flange and the deformable portion of the member has a smooth dome-like arrangement. It is also possible that the intermediate element is a dome like member having a central depression or dimple which receives a coupling element and the cover member has a dome-like portion engaging the coupling element for transferring its stroke to the intermediate element.

In each of the examples, the cover member and any of the intermediate elements are secured as a structural unit on a retaining ring which is removably connected to the head housing, preferably the retaining ring is threaded onto the head housing and the cover member and other members if present have peripheral flanges which are permanently engaged into the ring element.

Each of the embodiments of the improvement are particularly useful in a rotatable socket, which includes a hollow or tubular cylindrical shaft having a bore for receiving a tool from one end and having means for transmitting torque from the socket to the tool which means comprises a dog. The catch means for the socket preferably includes at least one support element extending parallel to the axis of the hollow cylindrical shaft and each support element has a catch nose or projection which extend radially inward for engagement in an annular groove provided in the shank of the tool which is to be disposed in the cylindrical shaft. Preferably, the hollow cylindrical shaft has an inner recess adjacent its bore for accepting the catch means and the recess enables or allows each of the support elements to be moved radially outward by the pressure surface during movement to the unlocking position.

BRIEF DESCRIPTION OF THE DRAWINGS

FIG. 1 is a cross-sectional view of a head housing of a dental handpiece containing a rotatable socket in accordance with the present invention;

FIG. 1a is a partial cross-sectional view taken on line Ia—Ia of FIG. 1 with a tool inserted in the socket of the housing;

FIG. 2 is a perspective view of a tool which will be supported in the rotatable socket of the head housing of the present invention;

FIG. 3 is a partial cross-sectional view of the head housing showing an embodiment of a thumb actuable purchase in accordance with the present invention;

FIG. 4 is a partial cross-sectional view of a head housing showing another embodiment of the thumb actuated purchase in accordance with the present invention;

DESCRIPTION OF THE PREFERRED EMBODIMENTS

Figure 6:
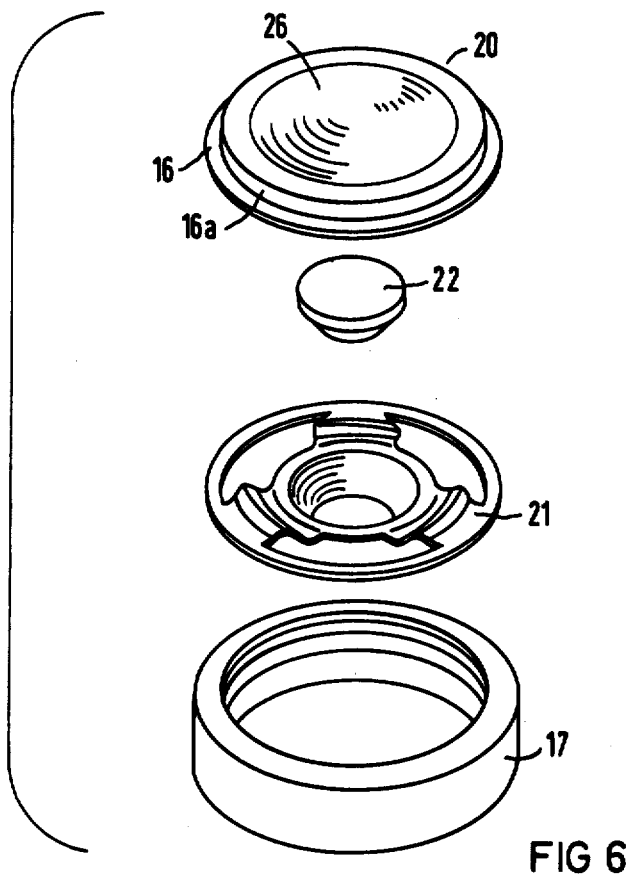
FIG. 6 is an exploded view of the thumb actuated purchase of FIG. 5.

The principles of the present invention are particularly useful in a rotatable socket generally indicated at 30 for rotatably supporting a tool 4 (FIG. 2) in a head part generally indicated at 1 in FIG. 1 of a dental handpiece. The head part 1 has a head housing 3 and has an adjacent neck portion or part 2 extending from one side.

As illustrated, the socket 30 has a hollow cylindrical shaft 6 which is supported for rotating in the housing 3 by two bearings 5 and 5a, which are illustrated as roller bearings. To rotate the shaft 6, the shaft 6 has a gear 31 which is in meshing relationship with the drive shaft 32 which is mounted for rotation in the neck part or portion 2 extending from the housing 3. The hollow shaft 6 adjacent one end has an enlarged recess 33 and receives a multiple slotted sleeve 7, which has at least one resilient tongue or support member 8 and 8a. Each of the tongues or support members at a position spaced inward from its free end has a catch nose or projection 9 or 9a which is urged into engagement in an annular groove 10 of the tool 4 (FIG. 2) after the tool, which may be a drill, a milling cutter or the like, has been inserted in the hollow shaft 6. In addition, the enlarged recess 33 has a dog 11, which engages a flat surface portion 12 at the end of the tool 4 to form means for transmitting torque between the rotatable socket and the tool. The various modifications of the support elements or tongues and of the hollow structure of the hollow shaft 6 are described in greater detail in the copending patent application Ser. No. 248,863 filed Mar. 30, 1981 and the disclosure of that copending application is incorporated by reference thereto.

Each of the resilient tongues or support elements 8, 8a which are diametrically arranged on the sleeve 7, extend essentially parallel to the axis of the shaft 6 with the free end terminating adjacent an upper portion of the free end of the head housing 3, which upper portion faces away from the tool outlet. The resilient tongues 8 and 8a are spaced from a pressure surface 13, which pressure surface is illustrated as being an internal surface of a cover member 14. The pressure surface 13 has a frusto-conical shape and is formed by an indentation which is located in the center of the cover member 14. The cover member 14 is part of a thumb actuated purchase which is actuated to move the tongues 8 and 8a radially outward to cause the projections or catch noses 9 and 9a to be withdrawn from the annular groove 10 of the tool 4.

The cover member 14 has an annular peripheral edge 16 extending from a cylindrical portion 16a and the peripheral edge 16 is secured in a retaining ring 17 preferably by being gripped in a groove which gripping occurs by flanging a portion of the ring 17. The retaining ring 17 is releasably secured on the housing 3 by being threaded thereon. Thus, the cover member 14 can be easily removed for example to enable replacing the sleeve 7 with the resilient tongues.

In the embodiment of FIG. 1, the portion of the cover member 14 which is surrounded by the cylindrical portion 16a has a dome shape such as a spherical convex shape with a centrally disposed indentation 15 which forms the frusto conical surface 13. Thus, depressing of the member 14 in the direction of arrow 34 will cause the pressure surface 13 to engage the resilient tongues 8 and 8a and move them to an unlocking position in the recess.

Another embodiment of the thumb actuated purchase is illustrated in FIG. 3. In this embodiment, a cover member 20 has a uniform spherical convex surface or shape and has its retaining edge or peripheral edge chucked or received in the ring 17. In addition to the cover member 20, a second element such as corrugated spring 21 is also chucked or fixed in the ring 17. Between the cover member 20 and the corrugated spring 21, a coupling member or connecting piece 22 is positioned and will transfer any motion of the cover member 20 to the corrugated spring 21 as the cover member is pressed in the direction of arrow 31. As illustrated, the corrugated spring 21 has a central depression 35 which receives the coupling member 22 and whose inner surface forms the pressure surface 36 which engages the tongues 8 and moves them to the unlocking position. As illustrated, the connecting piece 22 lies practically in point contact against the inner surface of the cover member 20.

Another embodiment of the thumb actuated purchase is illustrated in FIG. 4. In this embodiment, a corrugated spring 23 is provided with the cover member 20 and has a different configuration. The corrugated spring 23 is provided with a centrally disposed projection or outwardly extending indentation 24 which presses in a punctform against the internal surface of the cover member 20. Adjacent the indentation 24 is a reverse indentation 25 whose inner surface forms a pressure surface for engaging the free ends of the tongues 8 and 8a.

Another embodiment which is similar to the embodiment of FIG. 3 replaces the spring element 21 with an element having a shape similar to the member 14. Thus, the spring element will have a dome-like construction with a centrally disposed identation, which indentation will receive a coupling element similar to element 22. Thus, pressure placed by a thumb on a cover member such as 20 would be transferred by a coupling element to the spring element having a shape similar to the cover element 14.

Figure 5:
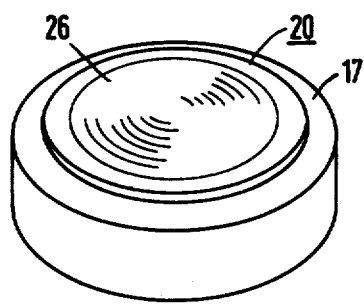
FIG. 5 is a perspective view of the thumb purchase of FIG. 3 removed from the housing of the head part.

In all of the embodiments, the cover element 14 or 20 respectively is preferably designed as a spring cover. In other words, either the cover member or respectively a portion of the member such as the dome-like portion 26 of FIGS. 5 and 6 exhibits a spring-like behavior with respect to the cylindrical portions 16a and the peripheral edge 16 which are rigidly secured to the head housing 3 either directly by gluing, welding or by the retaining ring 17 as illustrated. This spring-like behavior is obtained on the basis of the particular shaping of the member and/or on the type of material employed. For example the member 20 may be a cold worked spring steel with approximate thickness of 0.05 mm. If the appropriate radius of curvature has been selected for the particular material being used for the cover, this spring-like behavior which exists in the dome-like portion 26 of FIGS. 5 and 6, makes it possible for the dome to snap from the initial position illustrated with a convex dome into a concave portion after a certain pressure has been exceeded. Once the pressure from the thumb has been released, the spring-like nature of the cover member will cause the concave shape to snap towards the illustrated convex shape. A characteristic noise will also occur during this changing from the convex to the concave shape and it will basically occur as the center passes between the two positions and is usually at the point when the specific resistance has been overcome.

The stroke, which is generated by pressing against the cover member, is directed towards the retaining elements or resilient tongues 8 and 8a either directly by the pressure surface 13 or via the coupling piece, for example the element 22, to the pressure surface of the intermediate element to cause the particular tongues to be spreaded apart due to the conical shape of the pressure surface. This spreading apart will cause disengagement of the catch noses or projections from the annular groove 10 of the tool 4. When the pressure on the cover is released, the cover will return to its initial position and the coupling piece as well as any intermediate elements such as the corragated springs 21 or 23 will return to their initial position which is illustrated in the drawings.

Although various minor modifications may be suggested by those versed in the art, it should be understood that we wish to embody within the scope of the patent granted hereon, all such modifications as reasonably and properly come within the scope of our contribution to the art.

We claim:

1. In a rotatable socket for supporting a tool for rotation in a head housing of a dental handpiece, said socket having a bore for receiving a tool from one end, catch means for releasably retaining a tool in said bore, said catch means includes at least one catch member having a free end movable radially between a locking position engaged in the recess for retaining the tool in the bore of the socket and an unlocking position for releasing the tool, and a thumb actuated purchase disposed on the head housing, said purchase upon actuation engaging each catch member to radially move it to the unlocking position to allow removal of the tool from the socket, the improvements comprising the purchase having a pressure surface with an inclined portion of a predetermined shape and movable from a position disengaged from the free end of each catch member to a position engaging the free end of each catch member to cause radial movement to the unlocking position, a cover member having a peripheral edge, and means for rigidly securing the peripheral edge of the cover member to the head housing, said cover member having an elastically deformable portion movable through a stroke when pressure is applied to the purchase, so that upon applying pressure to the cover member, the deformable portion moves through the stroke to cause the pressure surface to engage the free end of each catch member and to move it radially to the unlocking position.

2. In a rotatable socket according to claim 1, wherein the elastically deformable portion of the cover member has a spherical shape providing a convex dome, said material of the cover member having a spring property enabling the convex dome to be converted into a concave dome and providing a reset power which automatically returns the dome portion to its initial configuration upon release of pressure.

3. In a rotatable socket according to claim 2, wherein the shape and the material of the cover member are selected so that upon the application of the pressure to the convex dome the portion moves through a center and then snaps into the concave dome and when the pressure is removed automatically snaps back to the convex dome.

4. In a rotatable socket according to claim 1, wherein the pressure surfaces is an inner surface of the cover member formed by a centrally disposed indentation in the cover member, and wherein the elastic portion of the cover member has a spring-like property so that upon release of pressure, said pressure surface moves to a rest position disengaged from the catch member.

5. In a rotatable socket according to claim 1, wherein the pressure surfaces are formed on an intermediate element rigidly secured to the housing between the cover member and housing, said intermediate element being a corrugated spring and a coupling element being disposed between the corrugated spring and the cover member for transferring movement to said spring and the pressure surfaces thereof.

6. In a rotatable socket according to claim 1, wherein the pressure surfaces are disposed on an intermediate element comprising a corrugated spring secured to the head housing, said corrugated spring having a centrally disposed indentation in contact with the cover member to enable transfer of movement of the cover member to said corrugated spring and the pressure surfaces thereof.

7. In a rotatable socket according to claim 1, wherein the cover member has a smooth spherical dome, said pressure surfaces being formed in an intermediate element having a domed configuration with a centrally disposed indentation forming the pressure surfaces, a coupling element received in the indentation of the intermediate element for transferring movement of the smooth dome of the cover member to the intermediate element as the cover member is pressed.

8. In a rotatable socket according to claim 1, wherein the means for securing the cover member onto the housing comprises a retaining ring releasably secured to the head housing.

9. In a rotatable socket according to claim 8, wherein the cover member is clamped in said retaining ring.

10. In a rotatable socket according to claim 8, wherein the retaining ring is threaded onto the head housing.

11. In a rotatable socket according to claim 1, wherein the pressure surfaces are provided on an intermediate member, said means for rigidly securing the peripheral edge of the cover member to the head housing comprising a retaining ring, said peripheral edges of the cover member and the intermediate member being connected to the retaining ring.

12. In a rotatable socket according to claim 1, wherein the socket includes a hollow cylindrical shaft having the bore for receiving the tool from one end thereof and having means for transmitted torque from the socket to the tool which has a flat surface adjacent one end and an annular groove, and each of said catch members being received in the hollow shaft and protruding from the other end thereof, each of the catch members being provided with a catch nose inward of the free end thereof for reception in the annular groove to hold the tool in said hollow shaft.

* * * * *